United States Patent
Dai et al.

(10) Patent No.: US 11,752,087 B2
(45) Date of Patent: Sep. 12, 2023

(54) ACTIVATED REVITALIZING LOTION AND PREPARATION METHOD AND APPLICATION THEREOF

(71) Applicants: Hebei Kangteng Biological Technology Co., Ltd., Tangshan (CN); Tangshan Jinrong Hospital, Tangshan (CN)

(72) Inventors: Jinrong Dai, Tangshan (CN); Xinran Liu, Tangshan (CN); Yanli Zuo, Tangshan (CN); Xiangyang Li, Tangshan (CN); Xiufen Chang, Tangshan (CN); Yuping Dai, Tangshan (CN)

(73) Assignees: Hebei Kangteng Biological Technology Co., Ltd., Tangshan (CN); TANGSHAN JINRONG HOSPITAL, Tangshan (CN)

( * ) Notice: Subject to any disclaimer, the term of this patent is extended or adjusted under 35 U.S.C. 154(b) by 106 days.

(21) Appl. No.: 17/502,557

(22) Filed: Oct. 15, 2021

(65) Prior Publication Data
US 2022/0313594 A1    Oct. 6, 2022

(30) Foreign Application Priority Data
Mar. 31, 2021    (CN) .......................... 202110354376.2

(51) Int. Cl.
A61K 8/98    (2006.01)
A61Q 19/00   (2006.01)
A61K 8/893   (2006.01)

(52) U.S. Cl.
CPC .............. *A61K 8/893* (2013.01); *A61Q 19/00* (2013.01); *A61K 2800/91* (2013.01)

(58) Field of Classification Search
None
See application file for complete search history.

(56) References Cited

U.S. PATENT DOCUMENTS

2010/0003270 A1*   1/2010   Kief .................. A61P 35/00
                                                        435/2

* cited by examiner

Primary Examiner — Brian Gulledge
(74) Attorney, Agent, or Firm — HoustonHogle LLP

(57) ABSTRACT

The present disclosure relates to the cosmetology field, in particular to an activated revitalizing lotion and its preparation method and application. A preparation method of an activated revitalizing lotion comprises the steps of: mixing an isolated blood sample, ozone-oxygen mixture and sodium citrate, and centrifuging the mixed blood sample at 1800-2000 r/min for 9-10 min to obtain a plasma supernatant for use as an activated revitalizing lotion; the ozone-oxygen mixture has an ozone concentration of 42.8-171.4 μg/L and added in an amount of 2.3-3.2 L/1 L of the isolated blood sample; and sodium citrate is added in an amount of 0.2-0.3 mg/1 L of the isolated blood sample. The activated revitalizing lotion prepared by the preparation method of the present disclosure shows improved effect in repair and revitalization of skin or subcutaneous tissues.

5 Claims, No Drawings

ACTIVATED REVITALIZING LOTION AND PREPARATION METHOD AND APPLICATION THEREOF

RELATED APPLICATION

This patent application claims the benefit and priority of Chinese Patent Application No. 202110354376.2 filed with China National Intellectual Property Administration on Mar. 31, 2021, the disclosure of which is incorporated by reference herein in its entirety as part of the present application.

TECHNICAL FIELD

The present disclosure relates to the cosmetology field, and particularly to an activated revitalizing lotion and its preparation method and application.

BACKGROUND ART

Platelet-rich plasma is plasma containing high-concentration platelets obtained by centrifuging autologous whole blood. The platelet-rich plasma is rich in a variety of growth factors, which plays an important role in promoting cell proliferation and differentiation, increasing collagen synthesis ability and promoting matrix synthesis and sedimentation. In addition, the growth factors coordinate with each well. Therefore, the platelet-rich plasma is often used in the repair and revitalization of skin or subcutaneous tissues.

The existing platelet-rich plasma is mostly collected from venous blood, in which the blood cells have a relatively low activation level, and the growth factors have a poor secretory activity. The effect needs to be improved, and there is also a risk of endogenous or exogenous infection induced by the blood.

SUMMARY

In order to improve the effect of the platelet-rich plasma in the repair and revitalization of skin or subcutaneous tissues, the present disclosure provides a preparation method of an activated revitalizing lotion.

In order to repair and revitalize skin or subcutaneous tissues, the present disclosure provides an activated revitalizing lotion.

In order to repair and revitalize skin or subcutaneous tissues, the present disclosure provides the use of the activated revitalizing lotion.

A preparation method of the activated revitalizing lotion provided in the present disclosure is implemented by the following technical solution.

A preparation method of an activated revitalizing lotion, comprising the steps of:

mixing an isolated blood sample, ozone-oxygen mixture and sodium citrate, and centrifuging the mixed blood sample to obtain a plasma supernatant for use as an activated revitalizing lotion;

wherein the ozone-oxygen mixture has an ozone concentration of 42.8-171.4 µg/L and used in an amount of 2.3-3.2 L/1 L of the isolated blood sample; and the sodium citrate is used in an amount of 0.2-0.3 mg/1 L of the isolated blood sample.

By adopting the above technical solution, the ozone-oxygen mixture is used to activate the isolated blood sample, stimulate the cells in the isolated blood sample, allowing secretion of a large number of growth factors, thereby improving the effect of plasma on promoting tissue regeneration and repairing problematic skin.

Meanwhile, the oxygen content in the activated plasma is increased, thereby improving oxygen supply for local tissue, accelerating the skin repair and improving the anti-aging effect.

On the other hand, some products decomposed by ozone under the action of enzymes in the plasma stimulate the balance of the immune system, reduce the possibility of edema (which can subside) caused by dermal injection and subcutaneous injection, and accelerate the subsiding of edema.

Therefore, the effect of the platelet-rich plasma is greatly improved when using it in the repair and revitalization of skin or subcutaneous tissues, the possibility of side effects caused by broken immune balance is also reduced, and risks of infection induced by endogenous or exogenous blood extrinsic infection is further reduced.

Further, the preparation method includes the steps of:

placing the isolated blood sample in a sterile bottle, and blowing a first ozone-oxygen mixture into the isolated blood sample, wherein the first ozone-oxygen mixture has an ozone concentration of 107.1-171.4 µg/L and added in an amount of 1.5-1.6 L/1 L of the isolated blood sample, resulting in a primary treated blood sample;

adding sodium citrate to the primary treated blood sample in an amount of 0.2-0.3 mg/1 L of the primary treated blood sample, and mixing well to obtain an anti-coagulated blood sample;

feeding a second ozone-oxygen mixture into the anti-coagulated blood sample in an ozone concentration of 42.8-171.4 µg/L and added in an amount of 0.8-1.6 L/1 L of the isolated blood sample, resulting in a secondary treated blood sample; and centrifuging the secondary treated blood sample to obtain a plasma supernatant for use as an activated revitalizing lotion.

By adopting the above technical solution, cells and growth factors in the blood are activated by the first ozone-oxygen mixture, so that more growth factors are metabolized by the cells in the blood. Sodium citrate is added for anticoagulation and to alleviate the residual ozone. Then the second ozone-oxygen mixture stimulates the plasma once again, so that more growth factors are released into the plasma. The inventor of the present disclosure believes that it may be due to the stimulation reaction of the cells induced by the second ozone-oxygen mixture, causing an destructive increase of the release rate of growth factors by the cells (the cell integrity is somewhat decreased after centrifugation by detecting the cell pellet). As a result, more growth factors are released and go into the plasma, and more growth factors are obtained in the finally obtained plasma.

Therefore, the effect of the platelet-rich plasma is greatly improved when using in the repair and revitalization of skin or subcutaneous tissues. At the same time, ozone is decomposed under the action of enzymes in the plasma and then centrifugation is conducted to yield the product, which promotes the balance of the immune system, slows down the stimulation of the immune system by the growth of other proteins (residues from cell damage) in the plasma, and reduces the possibility of edema (which can subside).

Further, the anti-coagulated blood sample is cultured in an incubator at 37° C. for 15-40 min after the anti-coagulated blood sample is obtained and before the secondary treated blood sample is obtained.

By adopting the above technical solution, more growth factors can be obtained from the plasma. As a result, the activated revitalizing lotion can achieve a better effect.

Further, the first ozone-oxygen mixture has an ozone concentration of 107.1-171.4 μg/L, and the first ozone-oxygen mixture is added in an amount of 1.5-1.6 L/1 L of the isolated blood sample, resulting in a primary treated blood sample; and the second ozone-oxygen mixture has an ozone concentration of 42.8-75 μg/L, and an amount of the second ozone-oxygen mixture is 0.8-0.9 L/1 L of the isolated blood sample.

By adopting the above technical solution, it is found through experiments by the inventor of the present disclosure that the decrease in the ozone-oxygen concentration in the second ozone-oxygen mixture can increase the protein content in the plasma and increase the total amount of growth factors, and the integrity rate of centrifuged residual cells is also slightly increased. The second ozone-oxygen mixture in the present disclosure stimulates the cells in anti-coagulated blood samples to release growth factors, which can be realized by multi-directional and multi-transmission paths (possibly allogeneic stimulation, cell rupture, etc.). Under the above conditions, a large number of growth factors are obtained, and the activated revitalizing lotion can achieve a good effect.

Further, the secondary treated blood sample is centrifuged for 9-10 min at 1800-2000 r/min.

By adopting the above technical solution, the content of growth factors features high content of isolated plasma and low content of miscellaneous proteins.

The activated revitalizing lotion provided in the present disclosure is achieved through the following technical solution.

The present disclosure provides an activated revitalizing lotion obtained by using the above preparation method for the activated revitalizing lotion, which is a non-gel liquid.

By adopting the above technical solution, the activated revitalizing lotion of the present disclosure has a good effect in the repair and revitalization of skin or subcutaneous tissues, also reduces the possibility of side effects caused by broken immune balance, and further reduces risks of endogenous or exogenous infection. The non-gel liquid is convenient for use, and the users feel better than gel filling and mesotherapy after use.

Further, the use of the activated revitalizing lotion includes the following steps:

pre-treating the skin on which the activated revitalizing lotion is applied, including cleaning and disinfection; and drawing the activated revitalizing lotion and applying it on the skin surface, where the penetration of the activated revitalizing lotion is promoted under pressure.

By adopting the above technical solutions, the activated revitalizing lotion has a better mitigating and regulating effect on skin abnormalities (acne scars, dry skin, redness and swelling) caused by new skin and allergies, and reduces scars and acne scars, relieves dry skin, redness and other epidermal allergies, and also has a certain regulating effect on the skin, which is weaker than injection.

Further, the use of the activated revitalizing lotion includes the following steps:

drawing the activated revitalizing lotion and injecting it into the dermis and/or the subcutaneous tissue of the skin, wherein the injection includes needle-free injection and puncture injection.

By adopting the above technical solution, the activated revitalizing lotion has a better repair effect on the skin dermis, especially for the face skin. The activated revitalizing lotion also regulates the facial skin and promotes the facial blood circulation to raise a person's spirits.

In summary, the present disclosure has the following beneficial effects:

1. The ozone-oxygen mixture is used to activate isolated blood samples, stimulate the cells in isolated blood samples to secrete a large number of growth factors, and improves the effect of plasma on promoting tissue regeneration and repairing problematic skin. At the same time, the oxygen content in the activated plasma is increased, the supply for local tissue is improved, the repair is accelerated, and the anti-aging effect is improved. On the other hand, some products decomposed by ozone under the action of enzymes in the plasma stimulate the immune system for balance, reduce the possibility of edema (which can subside) caused by dermal injection and subcutaneous injection, and accelerate the subsiding of edema. Therefore, the effect of the platelet-rich plasma is greatly improved when using in the repair and revitalization of skin or subcutaneous tissues, the possibility of side effects caused by broken immune balance is also reduced, and risks of endogenous or exogenous infection is further reduced.

2. The second ozone-oxygen mixture in the present disclosure stimulates the cells in anti-coagulation samples to release growth factors, which can be realized by multi-directional and multi transmission paths (possibly allogeneic stimulation, cell rupture, etc.). Under the above conditions, a large number of growth factors are obtained, and the activated revitalizing lotion can achieve a good effect. The first ozone-oxygen mixture activates cells and growth factors in the blood, so that the cells in the blood metabolize more growth factors. Sodium citrate is added for anti-coagulation, and to alleviate ozone residue, and then the second ozone-oxygen mixture stimulates the plasma again, so that more growth factors are released into the plasma. Therefore, the effect of the platelet-rich plasma is greatly improved when using in the repair and revitalization of skin or subcutaneous tissues; at the same time, some products decomposed by ozone under the action of enzymes in the plasma promote the balance of the immune system, slows down the stimulation of the immune system by the growth of other proteins (cell damage residues) in the plasma, and reduces the possibility of edema (which can subside).

3. The activated revitalizing lotion of the present disclosure has a good effect on repair and revitalization of skin or subcutaneous tissues, reduces the possibility of side effects caused by broken immune balance, and reduces risks of endogenous or exogenous infection.

4. The activated revitalizing lotion has a better mitigating and regulating effect on skin abnormalities (acne scars, dry skin, redness and swelling) caused by fresh skin and allergies, and reduces scars and acne scars, relieves dry skin, redness and other epidermal allergies, and also has a better repair effect on the skin dermis if injected into the dermis and/or the subcutaneous tissue of the skin, especially for the face skin. The activated revitalizing lotion also regulates the facial skin and promotes the facial blood circulation to raise a person's spirits.

DETAILED DESCRIPTION OF THE EMBODIMENTS

Animal Experiment 1

The experimental rabbit was depilated from the right hind leg to expose a 5 cm*5 cm bare skin surface (the skin surface was kept exposed during the experiment). The surface and part of the dermis were removed manually to make an incision of 1 cm*1 cm. When the incision heals and new skin grows at the incision, the skin was intact, and there was no pain sensation when coming in contact with the external, it was taken as the sample rabbit.

60 rabbits with incisions made in the same period were chosen and divided into a blank group 1, an experimental group A1 and a comparative experimental group B1, with 20 rabbits in each group.

Experimental Group A1

8 mL of the isolated blood sample was drawn from the sample rabbit, the first ozone-oxygen mixture was blown into the isolated blood sample and mixed, wherein the first ozone-oxygen mixture is added in an ozone concentration of 107.1 µg/L and in an amount of 1.6 L/1 L of the isolated blood sample, resulting in a primary treated blood sample;

sodium citrate was added to the primary treated blood sample in an amount of 0.2 mg/L the primary treated blood sample and mixed well to obtain an anti-coagulated blood sample, and the anti-coagulated blood sample was cultured in an incubator at 37° C. for 30 min;

the second ozone-oxygen mixture was fed into the anti-coagulated blood sample in an ozone concentration of 42.8 µg/L and an amount of 0.8 L/1 L of the isolated blood sample, resulting in a secondary treated blood sample; and the secondary treated blood sample was centrifuged to obtain a plasma supernatant for use as a test sample A1.

The incision of the sample rabbit was coated with the test sample A1, and acquirement of the isolated blood sample and coating of the test sample A1 were repeated at an interval of 5 days.

Comparative Experimental Group B1

8 mL of the isolated blood sample was drawn from the sample rabbit and centrifuged and separated to obtain a plasma supernatant for use as a test sample B1.

The incision of the sample rabbit was coated with the test sample B1, and acquirement of the isolated blood sample and coating of the test sample B1 were repeated at an interval of 5 days.

Blank Group 1

The incision of the sample rabbit was coated with normal saline, and the coating of normal saline was repeated at an interval of 5 days.

The recovery of skin at the incision of sample rabbits in blank group 1, experimental group A1 and comparative experimental group B1 was recorded. The average recovery date and recovery situations were recorded until the skin recovered to a same skin color such that the incision had a consistent skin color when seen with naked eyes, or to an extent that there was no need for further recovery or there was incomplete recovery.

The recovery of sample rabbits in the blank group 1, in the experimental group A1 and in the comparative experimental group B1 is shown in the table below.

TABLE 1

Recovery of sample rabbits in blank group 1, experimental group A1 and comparative experimental group B1

| | Recovery Day | Recovery at day 36 | Recovery at day 60 |
| --- | --- | --- | --- |
| Blank group 1 | * | The new growing skin at the incision was significantly different from | The new growing skin at the incision was significantly different from |

TABLE 1-continued

Recovery of sample rabbits in blank group 1, experimental group A1 and comparative experimental group B1

| | Recovery Day | Recovery at day 36 | Recovery at day 60 |
| --- | --- | --- | --- |
| | | the surrounding skin and scars were formed | the surrounding skin, and scars were formed |
| Experimental group A1 | day 34-36 | Consistent skin color with naked eyes | Consistent skin color with naked eyes |
| Comparative experimental group B1 | day 56-60 | The new growing skin at the incision was significantly different from the surrounding skin, and scars were formed | Consistent skin color with naked eyes |

Animal Experiment 2

The experimental rabbit was depilated from the right hind leg to obtain a 5 cm*5 cm bare skin surface (the skin surface was kept bare during the experiment). The surface and part of the dermis were removed artificially to make a wound. The size of the wound was 1 cm*1 cm. When the wound heals and new skin grows from the wound, after 35 days of healing, the experimental rabbit with scar was taken as the sample rabbit.

60 rabbits with wounds made in the same period were taken, and every 20 rabbits were divided into blank group 2, experimental group A2 and comparative experimental group B2.

Experimental Group A2

8 mL of the isolated blood sample was drawn from the sample rabbit, the first ozone-oxygen mixture was blown into the isolated blood sample and mixed, wherein the first ozone-oxygen mixture is added in an ozone concentration of 171.4 µg/L and in an amount of 1.5 L/1 L of the isolated blood sample, resulting in a primary treated blood sample;

sodium citrate was added to the primary treated blood sample in an amount of 0.3 mg/1 L of the primary treated blood sample and mixed well to obtain an anti-coagulated blood sample, and the anti-coagulated blood sample was cultured in an incubator at 37° C. for 30 min;

the second ozone-oxygen mixture was fed into the anti-coagulated blood sample in an ozone concentration of 75 µg/L, and an amount of 0.9 L/1 L of the isolated blood sample, resulting in a secondary treated blood sample; and the secondary treated blood sample was centrifuged to obtain a plasma supernatant for use as a test sample A2.

Sample rabbits were injected intracutaneously with 0.2 mL of test sample A2 around the wound, the isolated blood sample was repeatedly obtained at an interval of 5 days and the test sample A2 was repeatedly obtained for intracutaneous injection.

Comparative Experimental Group B2

8 mL of the isolated blood sample was drawn from the sample rabbit and centrifuged and separated to obtain a plasma supernatant for use as a test sample B2.

Sample rabbits were injected intracutaneously with 0.2 mL of test sample B2 around the incision, the acquirement of isolated blood sample and intracutaneous injection of the test sample B2 were repeated at an interval of 5 days.

Blank Group 2

Sample rabbits were injected intracutaneously with normal saline, and the intracutaneous injection of normal saline was repeated at an interval of 5 days.

The recovery of skin at the incision of sample rabbits in blank group 2, experimental group A2 and comparative experimental group B2 was recorded. The average recovery date and recovery situations were recorded until the skin recovered to a same skin color such that the incision had a consistent skin color when seen with naked eyes, or to an extent that there was no need for further recovery or there was incomplete recovery.

The recovery of sample rabbits in blank group 1, experimental group A1 and comparative experimental group B1 is shown in the table below.

TABLE 2

Recovery of sample rabbits in blank group 1, experimental group A1 and comparative experimental group B1

| | Recovery Day | Recovery at day 12 | Recovery at day 36 | Recovery at day 60 |
|---|---|---|---|---|
| Blank group 2 | * | Not changed | Not changed | Almost not changed |
| Experimental group A2 | day 31-33 | The scars became visibly lighter | consistent with the naked eye | Consistent skin color with naked eyes |
| Comparative experimental group B2 | day 47-59 | The scars are became visibly lighter | The scars became visibly lighte | Consistent skin color with naked eyes |

Example 1

20 mL of the isolated blood sample was placed in a sterile bottle, and a first ozone-oxygen mixture was blown into the isolated blood sample, wherein the first ozone-oxygen mixture has an ozone concentration of 128.6 μg/L and added in an amount of 1.5 L/1 L of the isolated blood sample, resulting in a primary treated blood sample.

Sodium citrate was added to the primary treated blood sample in an amount of 0.3 mg/1 L of the primary treated blood sample and mixed well to obtain an anti-coagulated blood sample, and the anti-coagulated blood sample was cultured in an incubator at 37° C. for 30 min.

The second ozone-oxygen mixture was fed into the anti-coagulated blood sample in an ozone concentration of 75 μg/L and in an amount of 0.8 L/1 L of the isolated blood sample, resulting in a secondary treated blood sample; and the secondary treated blood sample was centrifuged at 2000 r/min for 9 min to obtain a plasma supernatant for use an activated revitalizing lotion.

A newly healed wound on volunteers after surgery was applied the activated revitalizing lotion. After application, the acquirement of the isolated blood samples was repeated and the activated revitalizing lotion was applied at an interval of 5 days.

Another independent newly healed skin was taken from the postoperative wound as the control group.

20 mL of the blood sample was centrifuged at 2000 r/min for 9 min to obtain a plasma supernatant for use a comparison solution.

A newly healed wound on volunteers after surgery was applied the comparison solution. After application, the acquirement of the isolated blood samples was repeated and the comparison solution applied at an interval of 5 days.

Another independent newly healed skin was taken from the postoperative wound as a control group.

The time for which the skin color of the newly healed skin was consistent with that of the surrounding skin was taken as the result. Among them, the recovery time for the use of the activated revitalizing lotion was designated as the application recovery time, the recovery time for the use of the comparison solution was designated as the contrast recovery time, and the recovery time for the blank group was designated the natural recovery time.

The effect of the activated revitalizing lotion is shown in the table below.

TABLE 3

Recovery Date Table for Example 1

| | Volunteer age/year | Application recovery time/days | Contrast recovery time/days | Natural recovery time/days |
|---|---|---|---|---|
| Volunteer 1 | 25 | 27 | 42 | 53 |
| Volunteer 2 | 26 | 28 | 44 | 57 |
| Volunteer 3 | 27 | 30 | 49 | 64 |
| Volunteer 4 | 32 | 22 | 37 | 52 |
| Volunteer 5 | 36 | 30 | 46 | 56 |

Example 2

20 mL of the isolated blood sample was placed in a sterile bottle, and a first ozone-oxygen mixture was blown into the isolated blood sample, wherein the first ozone-oxygen mixture has an ozone concentration of 128.6 μg/L and added in an amount of 1.5 L/1 L of the isolated blood sample, resulting in a primary treated blood sample;

sodium citrate was added to the primary treated blood sample in an amount of 0.3 mg/1 L of the primary treated blood sample and mixed well to obtain an anti-coagulated blood sample, and the anti-coagulated blood sample was cultured in an incubator at 37° C. for 30 min.

The second ozone-oxygen mixture was fed into the anti-coagulated blood sample in an ozone concentration of 75 μg/L and in an amount of 0.8 L/1 L of the isolated blood sample, resulting in a secondary treated blood sample; and the secondary treated blood sample was centrifuged at 2000 r/min for 9 min to obtain a plasma supernatant for use as an activated revitalizing lotion.

The allergic dry skin on the volunteers was applied the activated revitalizing lotion. After application, the acquirement of the isolated blood samples was repeated and the activated revitalizing lotion was applied at an interval of 5 days.

Another independent allergic dry skin was taken from the postoperative wound as the control group.

20 mL of the isolated blood samples were centrifuged at a speed of 2000 r/min for 9 min to obtain a plasma supernatant for use as the comparison solution.

A postoperative allergic dry skin on the volunteers was applied the comparison solution. After application, the acquirement of the isolated blood samples was repeated and the comparison solution was applied at an interval of 5 days.

Another independent allergic dry skin was taken from the postoperative wound as a blank group.

The time for which the allergic dry skin was recovered was taken as the result. Among them, the recovery time of the use of the activated revitalizing lotion was designated as the application recovery time, and the recovery time for which another independent allergic dry skin was recovered was designated as the natural recovery time.

The effect of the activated revitalizing lotion is shown in the table below.

TABLE 4

Recovery Date Table for Example 2

| Volunteer | Volunteer age/year | Application recovery time/days | the contrast recovery time/days | Natural recovery date/days |
|---|---|---|---|---|
| Volunteer 6 | 22 | 12 | 14 | 19 |
| Volunteer 7 | 23 | 13 | 19 | 25 |
| Volunteer 8 | 35 | 14 | 9 | not recovered after 40 days |
| Volunteer 9 | 24 | 11 | 17 | 22 |
| Volunteer 10 | 32 | 12 | 18 | 23 |

It can be seen from Table 3 and Table 4 in Example 1 and Example 2 that the activated revitalizing lotion of the present disclosure produces a better effect on the repair and revitalization of skin or subcutaneous tissues and has a better mitigating and regulating effect on skin abnormalities (acne scars, dry skin, redness and swelling) caused by new skin and allergies, while it has a certain regulating effect on the skin.

Example 3

20 mL of the isolated blood sample were placed in a sterile bottle, and a first ozone-oxygen mixture was blown into the isolated blood sample, wherein the first ozone-oxygen mixture has an ozone concentration of 128.6 µg/L and added in an amount of 1.5 L/1 L of the isolated blood sample, resulting in a primary treated blood sample;

sodium citrate was added to the primary treated blood sample in an amount of 0.3 mg/1 L of the primary treated blood sample and mixed well to obtain an anti-coagulated blood sample, and the anti-coagulated blood sample was cultured in an incubator at 37° C. for 30 min;

the second ozone-oxygen mixture was fed into the anti-coagulated blood sample in an ozone concentration of 75 µg/L and in an amount of 0.8 L/1 L of the isolated blood sample, resulting in a secondary treated blood sample; and the secondary treated blood sample was centrifuged at 2000 r/min for 9 min to obtain a plasma supernatant for use as an activated revitalizing lotion.

1 mL of the activated revitalizing lotion was interdermally injected into the new skin growing at the volunteers' old wound scars (the scars were formed more than 45 days), the acquirement of the isolated blood samples was repeated interdermal injection of the activated revitalizing lotion was repeated at an interval of 5 days.

Another independent scar was taken from the postoperative wound as the control group.

20 mL of the isolated blood sample were centrifuged at a speed of 2000 r/min for 9 min to obtain a plasma supernatant for use as the comparison solution.

A postoperative old scar of volunteers was injected with 1 mL of the comparison solution. The acquirement of the isolated blood samples were repeated, and the comparison solution was injected at an interval of 5 days.

Another independent old scar was taken from the post-operative wound as the blank group.

The time for which the old scar was consistent with the surrounding skin under the naked eye. Among them, the recovery time of for the use of the activated revitalizing lotion was designated as the recovery time, the recovery time for the use of the comparison solution was designated as the contrast recovery date, and the recovery time for the blank group was designated as the natural recovery time.

The effect of the activated revitalizing lotion is shown in the table below.

TABLE 5

The effect of the activated revitalizing lotion

| Volunteer | Volunteer age/year | Application recovery time/days | Contrast recovery time/days | Natural recovery time/days |
|---|---|---|---|---|
| Volunteer 11 | 27 | 32 | 52 | not completely recovered at day 60 |
| Volunteer 12 | 27 | 37 | 53 | not completely recovered at day 60 |
| Volunteer 13 | 34 | 36 | 53 | not completely recovered within 60 days |
| Volunteer 14 | 22 | 30 | 49 | not completely recovered at day 60 |
| Volunteer 15 | 24 | 28 | 48 | not completely recovered at day 60 |

Volunteers' rejection on the day of injection is shown in the table below.

TABLE 6

Volunteers' rejection on the day of injection

| | Rejection on the day injected the activated revitalizing lotion | Rejection on the day injected the comparison solution |
|---|---|---|
| Volunteer 11 | No rejection | edema occurred after two injections, and edema disappeared after 1-2 days |
| Volunteer 12 | No rejection | Without rejection |
| Volunteer 13 | No rejection | edema occurred after one injection, and edema disappeared after 2 days |
| Volunteer 14 | No rejection | edema occurred after one injection, and edema disappeared after 3 days |
| Volunteer 15 | No rejection | No rejection |

It can be seen from Tables 4-6 in Examples 1-3 that, on one hand, the ozone-oxygen mixtures were used to activate the isolated blood samples, activate cells in the isolated blood samples to secrete a large number of growth factors, which improved the effect of the plasma on promoting tissue regeneration and repairing problematic skin. At the same time, the oxygen content in the activated plasma was increased, the local tissue supply was improved, the repair was accelerated, and the anti-aging effect was improved. On the other hand, some products decomposed by ozone under the action of enzymes in the plasma stimulated the balance of immune system, reduced the possibility of edema (which can subside) caused by dermal injection and subcutaneous injection, and accelerated the subsiding of edema. Therefore, the effect of the platelet-rich plasma was greatly improved when using in the repair and revitalization of skin or subcutaneous tissues, the possibility of side effects caused by broken immune balance was also reduced, and risk of endogenous or exogenous infection was further reduced.

Example 4

20 mL of the isolated blood sample were placed in a sterile bottle, and a first ozone-oxygen mixture was blown into the isolated blood sample in an ozone concentration of 171.4 µg/L and in an amount of 1.6 L/1 L of the isolated blood sample, resulting in a primary treated blood sample;

sodium citrate was added to the primary treated blood sample in an amount of 0.3 mg/1 L of the primary treated blood sample and mixed well to obtain an anti-coagulated blood sample, and the anti-coagulated blood sample was cultured in an incubator at 37° C. for 30 min;

the second ozone-oxygen mixture was fed into the anti-coagulated blood sample in an ozone concentration of 75 μg/L, and in an amount of 0.8 L/1 L of the isolated blood sample, resulting in a secondary treated blood sample; and the secondary treated blood sample was centrifuged at 2000 r/min for 9 min to obtain a plasma supernatant for use as an activated revitalizing lotion.

Examples 5-11

In Examples 5-11, the same isolated blood sample as that in Example 4 was used, except that the amount and the parameters for the activated revitalizing lotion were different, and the difference between Examples 5-11 and Example 4 lied in the concentration and the amount of the first ozone-oxygen mixture or the concentration and the amount of the second ozone-oxygen mixture, where the parameters are shown in the table.

TABLE 7

Parameters of the first ozone-oxygen mixture and the second ozone-oxygen mixture in Examples 4-11

| | | Ozone-oxygen concentration | Amount/L |
|---|---|---|---|
| Example 4 | the first ozone-oxygen mixture | 171.4 | 1.6 |
| | the second ozone-oxygen mixture | 75 | 0.8 |
| Example 5 | the first ozone-oxygen mixture | 150 | 1.5 |
| | the second ozone-oxygen mixture | 75 | 0.8 |
| Example 6 | the first ozone-oxygen mixture | 128.6 | 1.5 |
| | the second ozone-oxygen mixture | 75 | 1.5 |
| Example 7 | the first ozone-oxygen mixture | 128.6 | 1.5 |
| | the second ozone-oxygen mixture | 75 | 0.9 |
| Example 8 | the first ozone-oxygen mixture | 128.6 | 1.5 |
| | the second ozone-oxygen mixture | 42.8 | 0.8 |
| Example 9 | the first ozone-oxygen mixture | 128.6 | 1.5 |
| | the second ozone-oxygen mixture | 42.8 | 1.4 |
| Example 10 | the first ozone-oxygen mixture | 128.6 | 1.5 |
| | the second ozone-oxygen mixture | 75 | 1.5 |
| Example 11 | the first ozone-oxygen mixture | 128.6 | 1.5 |
| | the second ozone-oxygen mixture | 150 | 0.8 |

Comparative Example 1

The same isolated blood sample as that in Example 4 was used.

20 mL of the isolated blood samples were centrifuged at 2000 r/min for 9 min to obtain a plasma supernatant for use as a comparison solution.

The growth factor concentrations of the activated revitalizing lotion obtained in Examples 4-11 and in the comparison solution in Comparative Example 1 were measured. The concentration of the growth factor in the comparison solution of Comparative Example 1 was used as the benchmark and was recorded as 1. The concentration of the growth factor in the activated revitalizing lotion obtained in Examples 4-11 was expressed as a ratio of the concentration of the growth factor in the activated revitalizing lotion to the growth factor concentration of the comparison solution. The results are shown in the table below.

TABLE 8

Table for the measurement of concentrations of the growth factor in the activated revitalizing lotion obtained in Examples 4-11 and in the comparison solution in Comparative Example 1

| | growth factor concentration |
|---|---|
| Example 4 | 2.1 |
| Example 5 | 1.8 |
| Example 6 | 2.0 |
| Example 7 | 1.5 |
| Example 8 | 1.9 |
| Example 9 | 2.0 |
| Example 10 | 1.7 |
| Example 11 | 1.6 |
| Comparative Example 1 | 1 |

According to Table 8, the second ozone-oxygen mixture in the present disclosure can stimulate the cells in coagulation samples to release growth factors, which can be realized by multi-directional and multi transmission paths (possibly allogeneic stimulation, cell rupture, etc.). Under the above conditions, a large number of growth factors were obtained, and the activated revitalizing lotion can achieve a good effect. The first ozone-oxygen mixture activated cells and growth factors in the blood, so that more growth factors are metabolized by the cells in the blood. Sodium citrate was added for anticoagulation and to alleviate the residual ozone. Then the second ozone-oxygen mixture stimulated the plasma again, so that more growth factors were released into the plasma. Therefore, the effect of the platelet-rich plasma was greatly improved when using in the repair and revitalization of skin or subcutaneous tissues. At the same time, some products decomposed by ozone under the action of enzymes in the plasma promoted the balance of the immune system, slowed down the stimulation of the immune system by the growth of other proteins (residues from cell damage) in the plasma, and reduced the possibility of edema (which can subside).

Example 12

20 mL of the isolated blood sample (not from the same source as in Example 4) were placed in a sterile bottle, and a first ozone-oxygen mixture was blown into the isolated blood sample in an ozone concentration of 128.6 μg/L and in an amount of 1.5 L/1 L of the isolated blood sample, resulting in a primary treated blood sample; sodium citrate was added to the primary treated blood sample in an amount of 0.3 mg/1 L of the primary treated blood sample and mixed well to obtain an anti-coagulated blood sample, and the anti-coagulated blood sample was cultured in an incubator at 37° C. for 30 min;

the second ozone-oxygen mixture was fed into the anti-coagulated blood sample in an ozone concentration of 128.6 μg/L and in an amount of 0.8 L/1 L of the isolated blood sample, resulting in a secondary treated blood sample; and the secondary treated blood sample was centrifuged at 2000 r/min for 9 min to obtain a plasma supernatant for use as an activated revitalizing lotion.

Example 13

The same isolated blood sample as in Example 12 was used in Example 13.

20 mL of the isolated blood sample (not from the same source as in Example 4) were placed in a sterile bottle. The first ozone-oxygen mixture was extracted, wherein the first ozone-oxygen mixture has an ozone concentration of 128.6 μg/L, and an amount of the first ozone-oxygen mixture was 1.5 L/1 L of the isolated blood sample; and the second ozone-oxygen mixture was extracted, wherein the second ozone-oxygen mixture has an ozone concentration of 128.6 μg/L, and an amount of the first ozone-oxygen mixture was 0.8 L/1 L of the isolated blood sample. The extracted first ozone-oxygen mixture and second ozone-oxygen mixture were mixed well and blown into the isolated blood sample, resulting in a primary treated blood sample; sodium citrate was added to the primary treated blood sample and mixed well to obtain an anti-coagulated blood sample, wherein the amount of sodium citrate was 0.3 mg/1 L of the primary treated blood sample, and the anti-coagulated blood sample was cultured in an incubator at 37° C. for 30 min. The treated blood sample was centrifuged at 2000 r/min for 9 min to obtain a plasma supernatant for use as an activated revitalizing lotion.

Example 14

The same isolated blood sample as in Example 12 was used in Example 14. The difference was that the anti-coagulated blood sample was not cultured in an incubator at 37° C. for 30 min, while it was directly centrifuged after standing for 30 s to obtain the activated revitalizing lotion.

Example 15

The same isolated blood sample as in Example 12 was used in Example 15. The difference is that sodium citrate was not added, and the primary blood sample was directly treated by blowing into the second ozone-oxygen mixture, and the subsequent steps were continued.

Comparative Example 2

The same isolated blood sample as in Example 12 was used.
20 mL of the isolated blood sample were centrifuged at 2000 r/min for 9 min to obtain a plasma supernatant for use as a comparison solution.

The concentrations of growth factor in the activated revitalizing lotion obtained in Examples 12-15 and in the comparison solution in Comparative Example 2 were measured. The concentration of the growth factor in the comparison solution of Comparative Example 2 was used as a benchmark and was recorded as 1. The concentration of the growth factor in the activated revitalizing lotion obtained in Examples 12-15 was expressed as a ratio of the concentration of the growth factor in the activated revitalizing lotion to the concentration of the growth factor in the comparison solution. The results are shown in the table below.

TABLE 9

Measurement of concentrations of the growth factor in the activated revitalizing lotion obtained in Examples 12-15 and in the comparison solution in Comparative Example 2

| | growth factor concentration |
|---|---|
| Example 12 | 1.8 |
| Example 13 | 1.5 |
| Example 14 | 1.6 |
| Example 15 | 1.6 |
| Comparative Example 2 | 1 |

According to Table 9, after the anti-coagulated blood samples were obtained and before the secondary treated blood samples were obtained, the anti-coagulated blood samples were cultured in a 37° C. incubator for a period of time to obtain more growth factors in the plasma, and the better effect of the activated revitalizing lotion was obtained.

At the same time, the first ozone-oxygen mixture activated cells and growth factors in the blood, so that the cells in the blood metabolized more growth factors. Sodium citrate was added for anticoagulation, and to alleviate residual ozone, and then the second ozone-oxygen mixture stimulated the plasma again, so that more growth factors were released into the plasma. The inventor of the present disclosure believed that it may be due to the stimulation reaction of the cells induced by the second ozone-oxygen mixture, causing an destructive increase of the release rate of growth factors by the cells (the cell integrity was somewhat decreased after centrifugation by detecting the cell pellet). As a result, more growth factors were released and went into the plasma, and more growth factors were obtained in the finally obtained plasma.

Therefore, the effect of the platelet-rich plasma was greatly improved when using in the repair and revitalization of skin or subcutaneous tissues. At the same time, ozone was decomposed under the action of enzymes in the plasma and then centrifuged to obtain the product, which promoted the balance of the immune system, slowed down the stimulation of the immune system by the growth of other proteins (residues from cell damage) in the plasma, and reduced the possibility of edema (which can subside).

These examples of the present disclosure are merely explanatory but not restrictive. Those skilled in the art may make modifications without making creative contribution to these examples as needed after reading this specification. However, these modifications should be protected by the Patent Law as long as they fall within the scope of the claims of the present disclosure.

What is claimed is:

1. A method for preparing an activated revitalizing lotion, comprising the steps of:
    mixing an isolated blood sample, an ozone-oxygen mixture and sodium citrate, and centrifuging the mixed blood sample to obtain a plasma supernatant for use as an activated revitalizing lotion;
    wherein the ozone-oxygen mixture has an ozone concentration of 42.8-171.4 μg/L and a first ozone-oxygen mixture is added in an amount of 2.3-3.2 L/1 L of the isolated blood sample; and
    sodium citrate is added in an amount of 0.2-0.3 mg/1 L of the isolated blood sample.

2. A method for preparing an activated revitalizing lotion, comprising the steps of:
    placing the isolated blood sample in a sterile bottle, and blowing a first ozone-oxygen mixture into the isolated blood sample in an ozone concentration of 107.1-171.4 μg/L and in an amount of 1.5-1.6 L/1 L of the isolated blood sample, resulting in a primary treated blood sample;
    adding sodium citrate to the primary treated blood sample in amount of 0.2-0.3 mg/1 L of the primary treated blood sample, and mixing well to obtain an anti-coagulated blood sample;
    feeding a second ozone-oxygen mixture into the anti-coagulated blood sample in an ozone concentration of 42.8-171.4 μg/L and in an amount of 0.8-1.6 L/1 L of the isolated blood sample, resulting in a secondary treated blood sample; and centrifuging the secondary treated blood sample to obtain a plasma supernatant for use as an activated revitalizing lotion.

3. The method according to claim 2, wherein after the anti-coagulated blood sample is obtained and before the secondary treated blood sample is obtained, the anti-coagulated blood sample is cultured in an incubator at 37° C. for 15-40 min.

4. The method according to claim 2, wherein the first ozone-oxygen mixture has an ozone concentration of 128.6-150 µg/L, and the first ozone-oxygen mixture is added an amount of 1.5-1.6 L/1 L of the isolated blood sample, resulting in a primary treated blood sample; and the second ozone-oxygen mixture has an ozone concentration of 42.8-75 µg/L and the second ozone-oxygen mixture is added in an amount of 0.8-0.9 L/1 L of the isolated blood sample.

5. The method according to claim 2, wherein the secondary treated blood sample is centrifuged for 9-10 min at 1800-2000 r/min.

\* \* \* \* \*